(12) United States Patent
Stephan et al.

(10) Patent No.: US 9,384,543 B2
(45) Date of Patent: Jul. 5, 2016

(54) METHOD AND APARRATUS FOR CHARACTERIZING A PERSON'S SKIN IMPERFECTIONS

(75) Inventors: Sandrine Stephan, Beaugency (FR); Delphine Pelle de Queral, Ingre (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 525 days.

(21) Appl. No.: 12/762,853

(22) Filed: Apr. 19, 2010

(65) Prior Publication Data

US 2010/0271470 A1 Oct. 28, 2010

(30) Foreign Application Priority Data

Apr. 23, 2009 (FR) ...................................... 09 52660

(51) Int. Cl.
*A61B 5/00* (2006.01)
*G06T 7/00* (2006.01)
(52) U.S. Cl.
CPC ............. *G06T 7/0012* (2013.01); *A61B 5/0077* (2013.01); *A61B 5/411* (2013.01); *A61B 5/442* (2013.01); *A61B 5/444* (2013.01); *A61B 5/445* (2013.01); *G06T 2207/20212* (2013.01); *G06T 2207/30088* (2013.01)
(58) Field of Classification Search
None
See application file for complete search history.

(56) References Cited

U.S. PATENT DOCUMENTS 5,976,853 A * 11/1999 Guthridge et al. ............ 435/196
6,551,982 B1 4/2003 Ricci et al.
2004/0267102 A1 * 12/2004 Skladnev et al. .............. 600/315
2007/0086651 A1 * 4/2007 Stephan .................. A61B 5/442
382/162
2007/0248948 A1 * 10/2007 Hatzis et al. ....................... 435/4
2008/0058642 A1 * 3/2008 Gould ............................ 600/436

FOREIGN PATENT DOCUMENTS

| EP | 1 314 395 A2 | 5/2003 |
| FR | 2 891 641 | 4/2007 |
| WO | WO 00/67398 | 11/2000 |
| WO | WO 2007/042708 A1 | 4/2007 |

OTHER PUBLICATIONS

Claridge et al., "Modelling of edge profiles in pigmented skin lesions," *Medical Image Understanding and Analysis* (2002): 53-56. XP002571583.
Cotton et al., "Noninvasive skin imaging," *Information Processing in Medical Imaging. 15th International Conference* (1997): 501-506. XP0025781584.
French Search Report mailed on Mar. 5, 2010 for priority French application FR 0952660.

* cited by examiner

*Primary Examiner* — Mikhail Itskovich
(74) *Attorney, Agent, or Firm* — Merchant & Gould P.C.

(57) ABSTRACT

A method of characterizing a person's skin imperfections uses a digital color image-taking device to take at least one digital image of an area of skin including at least one imperfection to be characterized. An apparatus for characterizing the imperfections of the skin and a method for measuring the effectiveness of a treatment for skin imperfections use an active cosmetic, dermatological or pharmaceutical agent and further measure the effectiveness of a staining method aiming to attenuate or mask skin imperfections.

19 Claims, 3 Drawing Sheets

METHOD AND APARRATUS FOR CHARACTERIZING A PERSON'S SKIN IMPERFECTIONS

BACKGROUND OF THE INVENTION

The invention relates to a method and an apparatus for characterizing skin imperfections and its application in a method of assessing the effectiveness of a treatment for skin imperfections using a cosmetic, dermatological or pharmaceutical agent.

STATE OF THE ART

The document U.S. Pat. No. 6,551,982 B1 discloses a method and apparatus for the non-invasive estimation of a relative age of a person based on a near infrared method, called NIR, that uses a wavelength in the 700 to 2500 nanometer range.

Also, the document WO 00/67398 A1 discloses imaging systems and methods for analyzing the skin that implement the acquisition and the creation of various digital images in order to view skin defects, and then take into account a sub-image containing the skin defect.

Also, the document WO 2007/042 708, filed by the Applicant, discloses a method and apparatus for characterizing skin imperfections and a method of assessing the anti-aging effect of a cosmetic product.

AIMS OF THE INVENTION

The aim of the present invention is to resolve the technical problem involved in providing a novel method and a novel apparatus for characterizing skin imperfections.

The present invention also aims to resolve the technical problem involved in providing a method of assessing the effectiveness of an active cosmetic, dermatological or pharmaceutical agent or of a cosmetic, dermatological or pharmaceutical composition including said active agent on said imperfections, that implements the method or the apparatus for characterizing skin imperfections.

The present invention provides a satisfactory solution to these two technical problems, that is capable of providing greater accuracy in the characterization of said imperfections, relatively easy to implement, and safe and reliable with respect to the result obtained.

SUMMARY OF THE INVENTION

Definitions of Terms or Expressions Used According to the Invention

The expression "skin imperfections" should be understood to mean skin imperfections that are apparent or visible to the naked eye, or for which it is possible to take at least one image thereof by any image-taking method or device, for example a camera, a camcorder, possibly with the use of an image enlarging device.

Several types of skin imperfections that can be characterized by the method according to the invention can be identified.

First of all, there are the skin imperfections that result from various cutaneous dyschromias that take the form of at least one spot of different color from the healthy skin because of an abnormal pigmentation.

There are then the imperfections that result from the aging of the skin, whether intrinsic, as a consequence of genetically programmed senescence, or extrinsic, the consequence of excessive chemical or physical stimulations (exposure to the sun, to light, to UV, stress and malnutrition) that degrade the normal functions of the skin, and that are reflected in the appearance of rugae, wrinkles, spots, shadows, loose skin areas.

Finally, there are the imperfections that result from an irritation or an infection of the skin.

The expression "gray level" should be understood to mean the quantization of the light intensity picked up on a pixel of the digital sensor of the digital color image-taking device.

The expression "thresholding of the gray levels" should be understood to mean the elimination of the gray levels below a certain predetermined gray level threshold, in order to eliminate parasitic elements or artefacts.

The expression "representative group" should be understood to mean a group of people representative of a population of given age, and which is used to establish meaningful statistical results concerning the effectiveness of a treatment agent or product, in the context of the implementation of the invention.

According to a first aspect, the present invention provides a method of characterizing a person's skin imperfections, comprising the following steps:

a) a digital color image-taking device is used to take at least one digital image of an area of skin including at least one imperfection to be characterized, said image being defined by a multiplicity of pixels, that is transmitted to a digital image processing device;

b) the digital image is divided up into three color planes: red, green, blue, called R, G, B, using said image processing device;

c) just one of these planes or a combination of these planes is extracted;

said method being characterized by the fact that:

d) an imperfection is detected on the extracted plane or the combination of these planes;

e) there is defined, on said plane or said combination of these planes, an origin point O in relation to said imperfection, from which a straight line segment passing at least partly through an area of the imperfection is plotted;

f) n points P, denoted $P_1, P_2 \ldots P_n$, n being an integer greater than or equal to 2, are defined on said segment, at least one of these points, denoted $P_1$, being situated within the imperfection;

g) for each duly defined point P, a pair of values (x; y) is determined, x being the distance of said point P relative to the origin point O, y being the value of the gray level recorded at said point P;

h) each point P defined by its pair (x; y) is placed in an orthonormed frame of reference, in which the x axis represents said distances and the y axis represents the gray level, or vice versa;

i) for each segment defined at step e), defining, tracing or plotting a straight line, notably by the least squares method, from the different points $P_1$, to $P_n$ in said orthonormed frame, and calculating the slope of the obtained straight line, in order to characterize the imperfection.

The absolute value of the gradient can be used to characterize the intensity of the cutaneous imperfection all along the segment being studied.

A gray level variation registered by the image-taking appliance between the healthy skin and an area of the imperfection may reflect a variation of the skin tone, for example in the case of a pigment spot or a lesion, or even a characteristic relief of a ruga.

A high absolute gradient value indicates a major variation of the gray levels along the segment passing through the cutaneous imperfection, characteristic of a non-uniform skin tone or of a surface area having a roughness or a significant relief.

According to a particular embodiment of this method, said method is characterized in that each point O, $P_1, P_2 \ldots P_n$ corresponds to a pixel of the image.

According to another particular embodiment of this method, said method is characterized in that the gray levels are thresholded in order to determine the edge of the imperfection, denoted (BI) in the present application; the convex envelope of the imperfection is also determined in order to establish the origin point O within said imperfection, before plotting the segment.

According to this embodiment, it is also possible to determine a particular area, called "crown" of the imperfection, denoted (CI), the inner edge (BIC) and the outer edge (BEC) of which, situated either side of the edge (BI) of said imperfection, are plotted at a distance defined by the operator corresponding to a selected number of pixels from the edge of the imperfection (BI).

According to another particular embodiment of this method, said method is characterized in that the point $P_2$ is situated on the edge (BI) of the imperfection or outside the imperfection in the vicinity of the edge of the imperfection.

According to another particular embodiment of this method, said method is characterized in that there are defined on said first straight line segment a point $P_1$ situated on the inner edge of the crown (BIC), a point $P_2$ situated on the edge of the imperfection (BI), and a point $P_3$ situated on the outer edge of the crown (BEC).

According to yet another particular embodiment of this method, said method is characterized by defining, tracing or plotting, from the origin point O, several other straight line segments distinct from the first segment defined at step e), and passing at least partly through an area of the imperfection; then reproducing the steps f) to i) to obtain as many slope values as there are plotted segments, slope values from which the average is calculated to characterize the imperfection.

According to a particular variant of the latter embodiment, the method according to the invention is characterized in that, from a so-called horizontal axis, preferentially consisting of the first plotted segment, the other straight line segments are defined, traced or plotted in such a way that each of them forms, with said horizontal axis, a predetermined angle that is a multiple of THETA, said angle THETA being an angle, defined by the operator, greater than zero and less than 360°.

According to a preferred variant, THETA is a sub-multiple of 360, in particular lower or equal to 60°.

According to another particular embodiment of this method, said method is characterized by selecting, notably for an irregular spot, a THETA value ranging between 0.1 and 60°, better between 1 and 60°, in order to plot segments passing through the imperfection, in a sufficient number to characterize it well as an average.

According to yet another particular embodiment of this method, said method is characterized in that the blue color plane is extracted.

According to a particular characteristic of the method according to the invention, said method is characterized in that said image obtained by the digital color image-taking device is enlarged, to enable an operator to better view the skin imperfections and assess the thresholding of the gray levels with which to eliminate the parasitic elements or artefacts.

According to yet another particular embodiment of this method, said method is characterized in that a limited surface area of the skin of the person to be analyzed is selected, on which the skin imperfections are analyzed over the whole of this surface area.

According to another particular embodiment of the method according to the invention, said method is characterized in that either a digital color photographic appliance of good resolution available on the market, or a digital color camera of MONO-CCD, DI-CCD or TRI-CCD type, for example the Fotofinder™ camera from DEKA that has an image resolution of 450 000 pixels with 4 V LED built-in lighting, or a color camera available on the market, notably from SONY, is used as digital color image-taking device.

According to a particular embodiment of this method, said method is characterized in that the imperfection is a cutaneous dyschromia in the form of at least one spot of different color from the healthy skin because of an abnormal pigmentation, which results notably from the cutaneous effects of photodermatoses, from the pigmentation induced by contact dermatoses or medicinal photodermatoses, or even by melasma, keratoses, for example senile or actinic, senile lentigo (aging spots), solar lentigo, the persistent effects of burns, such as sunburns and other skin wounds, or scars, spots due to allergic or phototoxic reactions, dermatitis or other similar small fixed pigmented lesions; or the depigmented areas induced by certain leucodermias such as vitiligo.

According to another particular embodiment of this method, said method is characterized in that the imperfection is a ruga, a wrinkle, a shadow, an area of loose skin, resulting from the intrinsic or extrinsic aging of the skin.

According to another particular embodiment of this method, said method is characterized in that the imperfection is a lesion resulting from an irritation or a cutaneous infection, notably a dermatitis such as eczema for example.

According to yet another particular embodiment of the method on the invention, said method is characterized in that at least one image or a plurality of images of the skin of one and the same person is stored on a digital data storage device.

According to a second aspect, the invention relates to an apparatus for characterizing a person's skin imperfections, comprising:

a) a digital color image-taking device for taking at least one digital image of an area of skin including at least one imperfection to be characterized, said image being defined by a multiplicity of pixels, that is transmitted to a digital image processing device;

b) means of dividing up the digital image into three color planes: red, green, blue, called R, G, B, using said image processing device;

c) means of extracting just one of these planes or a combination of these planes;

said apparatus comprising:

d) means of detecting an imperfection on the extracted plane or the combination of these planes;

e) means of creating an origin point O in relation to said imperfection, means for plotting a straight line segment passing at least partly through an area containing the imperfection;

f) means of creating n points P on said segment, said points being denoted $P_1, P_2 \ldots P_n$, n being an integer greater than or equal to 2, at least one of these points, denoted $P_1$, being situated within the imperfection;

g) means of measuring and storing the distance of said point P relative to the origin point O; means of measuring and storing the gray level at said point P;

h) means of transferring the distances and the gray levels measured and stored for each point P, in an orthonormed frame of reference, in which the x axis represents said distances and the y axis the gray level, or vice versa;

i) for each segment defined at step e), calculating means for defining, tracing or plotting a straight line, notably by the least squares method, from the different points $P_1$, to $P_n$ in said orthonormed frame, and for calculating the slope of the obtained straight line, in order to characterize the imperfection.

According to a particular variant embodiment of the apparatus according to the invention, said apparatus is characterized in that the abovementioned means of selecting points are designed so that each point O, $P_1, P_2 \ldots P_n$ corresponds to a pixel of the image.

According to a particular embodiment of the apparatus according to the invention, said apparatus is characterized in that it comprises means of taking into account a thresholding of the gray levels; means of determining the convex envelope of the imperfection and of storing an origin point, possibly fixed by the operator, within said convex envelope, before plotting the segment.

According to another particular embodiment of the apparatus according to the invention, said apparatus is characterized in that there are defined on said first straight line segment a point $P_1$ situated on the inner edge of the crown (BIC), a point $P_2$ situated on the edge of the imperfection (BI), and a point $P_3$ situated on the outer edge of the crown (BEC).

According to a particular embodiment of the apparatus according to the invention, said apparatus is characterized in that it comprises calculation means for defining, tracing or plotting, from the origin point O, several other straight line segments distinct from the first segment and passing at least partly through an area of the imperfection; then for reproducing the steps f) to i), to obtain as many slope values as there are plotted segments, slope values from which the average is calculated in order to characterize the imperfection.

According to a variant embodiment, these calculation means are used, based on a so-called horizontal axis, preferentially consisting of the first straight line segment plotted, to define, trace or plot other straight line segments in such a way that each of them forms, with said horizontal axis, a predetermined angle that is a multiple of THETA, said angle THETA being an angle, defined by the operator, greater than zero and less than 360°, in particular lower or equal to 60°.

According to an advantageous characteristic of the apparatus of the invention, said apparatus is characterized in that it comprises means of enlarging said image obtained by the digital color image-taking device enabling an operator to better view the skin imperfections and assess the thresholding of the gray levels with which to eliminate the parasitic elements or artefacts.

According to a particular variant embodiment, this apparatus is characterized in that it comprises means for extracting, from an image of an area of the skin, taken by means of the image-taking device, an area of interest selected from said digital image.

According to an advantageous embodiment of the apparatus according to the invention, this apparatus is characterized in that it comprises means of illuminating the skin surface for which the digital image is being taken.

According to an advantageous embodiment of the apparatus according to the invention, said apparatus is characterized in that a digital color image-taking device is provided, selected from a digital color photographic appliance or a digital color camera, as defined in the present description.

According to a particular embodiment of the apparatus according to the invention, said apparatus is characterized in that it comprises means for storing at least one image or a plurality of images of the skin of one and the same person, on a digital data storage device.

According to yet another particular embodiment of the apparatus according to the invention, said apparatus is characterized in that it comprises a computer combined with a monitor comprising a screen, a keyboard and a mouse, and including software incorporating all the abovementioned means including:

means of dividing up the digital image into three color planes: red, green, blue, called R, G, B;

means of extracting just one of these planes; particularly the so-called blue plane corresponding to the blue color;

means of detecting an imperfection on the extracted plane or the combination of these planes;

means of creating an origin point O in relation to said imperfection, means for plotting at least a first straight line segment passing at least partly through said area including the imperfection;

means of creating n points P on said segment, said points being denoted $P_1, P_2 \ldots P_n$, n being an integer greater than or equal to 2;

means of measuring and storing the distance of said point P relative to the origin point O; means of measuring and storing the gray level at said point P;

means of transferring the distances and the gray levels measured and stored for each point P, in an orthonormed frame of reference, in which the x axis represents said distances and the y axis the gray level, or vice versa;

means for defining, tracing or plotting a straight line, notably using the least squares method, and for calculating the slope of the straight line obtained, in order to characterize the imperfection;

means for taking into account a thresholding of the gray levels;

possibly means of enlarging said image;

means of storing at least one image or a plurality of images of the skin.

According to a particular embodiment of the apparatus according to the invention, said apparatus is characterized in that it comprises calculation means for defining, tracing or plotting, from the origin point O, several other straight line segments distinct from the first segment and passing at least partly through an area of the imperfection; then for reproducing the same steps as for the first segment to obtain as many slope values as there are defined, traced or plotted segments, slope values from which the average is calculated in order to characterize the imperfection.

According to an advantageous, inventive method of relating the method and the apparatus for characterizing skin imperfections, the calculation means calculate the imperfection resulting from at least one pigment spot.

According to a third aspect, the present invention provides a method of measuring the effectiveness of a treatment of skin imperfections using an active cosmetic, dermatological or pharmaceutical agent or a cosmetic, dermatological or pharmaceutical composition including said active agent, comprising:

a) the characterization of at least one imperfection according to the method previously described as or resulting from the following description;

b) after having performed a cosmetic, dermatological or therapeutic treatment of said imperfection using at least said active agent or said composition, the characterization of the treated imperfection according to the method previously described or as resulting from the following description;

c) the comparison between the two characterizations to determine the effectiveness of said treatment, this comparison including the calculation of the slope or of the average of the slopes deduced from the characterization method; and d) the determination of the significant nature of the effectiveness of said treatment with regard to said imperfection, by comparing, using a statistical test, the variations of the slopes or of the averages of the above slopes before and after the treatment.

According to a particular embodiment of the method, said method is characterized in that the imperfection results from a cutaneous dyschromia, from the intrinsic or extrinsic aging of the skin or even from an irritation or an infection of the skin.

According to other variants, the method is in particular characterized in that the imperfection is:

a cutaneous dyschromia taking the form of a spot of different color from the healthy skin because of an abnormal pigmentation, resulting notably from the cutaneous effects of photodermatoses, of the pigmentation induced by contact dermatoses or medicinal photodermatoses, or even by melasma, keratoses, for example senile or actinic, senile lentigo (aging spots), solar lentigo, the persistent effects of burns, such as sunburns and other skin wounds, or scars, spots due to allergic or phototoxic reactions, dermatitis or other similar small fixed pigmented lesions; or the depigmented areas induced by certain leucodermias such as vitiligo, or a ruga, a wrinkle, a shadow, an area of loose skin, or even a skin lesion resulting from an irritation or a cutaneous infection, notably a dermatitis such as eczema for example.

The effectiveness of the treatment applied to the cutaneous imperfection is judged when at least one of the parameters concerned has reduced significantly after the treatment applied.

According to an advantageous embodiment of this method, said method is characterized in that the significant reduction is obtained with an error probability less than or equal to 5%.

According to a particular variant embodiment of the method, the parameters of the second image of the same area of skin obtained after treatment are compared against the parameters of the first skin image before treatment.

According to another advantageous embodiment of this method, the method of measuring the effectiveness of a treatment of skin imperfections is applied to a group of people presenting the imperfection to be treated. In this case, the average of the parameter deduced from the characterization method is calculated for all the people in the group, before and after treatment.

According to another particular variant embodiment of the method, the characterization of the imperfection includes the measurement of one or more points comprising $P_1$, situated within the imperfection, and $P_2$, situated on the edge of the imperfection or outside the imperfection in the vicinity of the edge of the imperfection.

According to another advantageous embodiment of this method, said method is characterized in that the effectiveness of an active cosmetic or dermatological agent or of a cosmetic or dermatological composition including said active agent is assessed over a panel of people from a group representative of a given age category, in order to determine the significance of the effectiveness of said active agent or of said composition with respect to said skin imperfection.

According to a fourth aspect, the present invention provides a method of measuring the effectiveness of the attenuation or the masking of skin imperfections, notably of a pigment spot, by a cosmetic staining composition, wherein:

at least one first digital image is taken, before the staining composition is applied, of an area of skin including an imperfection in order to determine the reference parameters of the skin before the application of the staining composition while taking into account at least the slope or the average of the above slopes;

at least one second image is taken after the staining composition is applied, and the same parameters are determined;

the parameters of the second image of the same area of skin obtained after application of the staining composition are compared against the parameters of the first skin image before application of said composition;

the positive effectiveness of the masking or attenuation effect obtained is concluded when at least one of the average parameters concerned that takes into account at least the slope or the average of the above slopes has reduced significantly compared to the average of the parameters of the first image.

According to a particular embodiment of the method, the cutaneous imperfection is a pigment spot.

In this case, the color used to stain the imperfection should match as closely as possible the tone of the skin surrounding the cutaneous imperfection so that, once the imperfection is masked or attenuated, the slope of the straight line calculated according to the characterization method described previously approaches zero, that is to say show a uniformity of tone over the entire segment from the origin point to the area passing through the cutaneous imperfection.

Various variant embodiments of the apparatus or of each method of measuring the effectiveness of a treatment of imperfections clearly emerge for those skilled in the art from the various embodiments of the first embodiment of the method of characterizing imperfections described previously or resulting from the following description complemented by the drawings that form an integral part of the invention.

By virtue of the methods and the apparatus according to the invention, the technical problems stated previously are resolved in a simple, safe and reliable way.

Other aims, characteristics and benefits of the invention will become clearly apparent in light of the explanatory description that follows, given with reference to a currently preferred embodiment of the invention.

DETAILED DESCRIPTION OF THE CURRENTLY PREFERRED EMBODIMENTS OF THE INVENTION

Example 1

Figure 1:
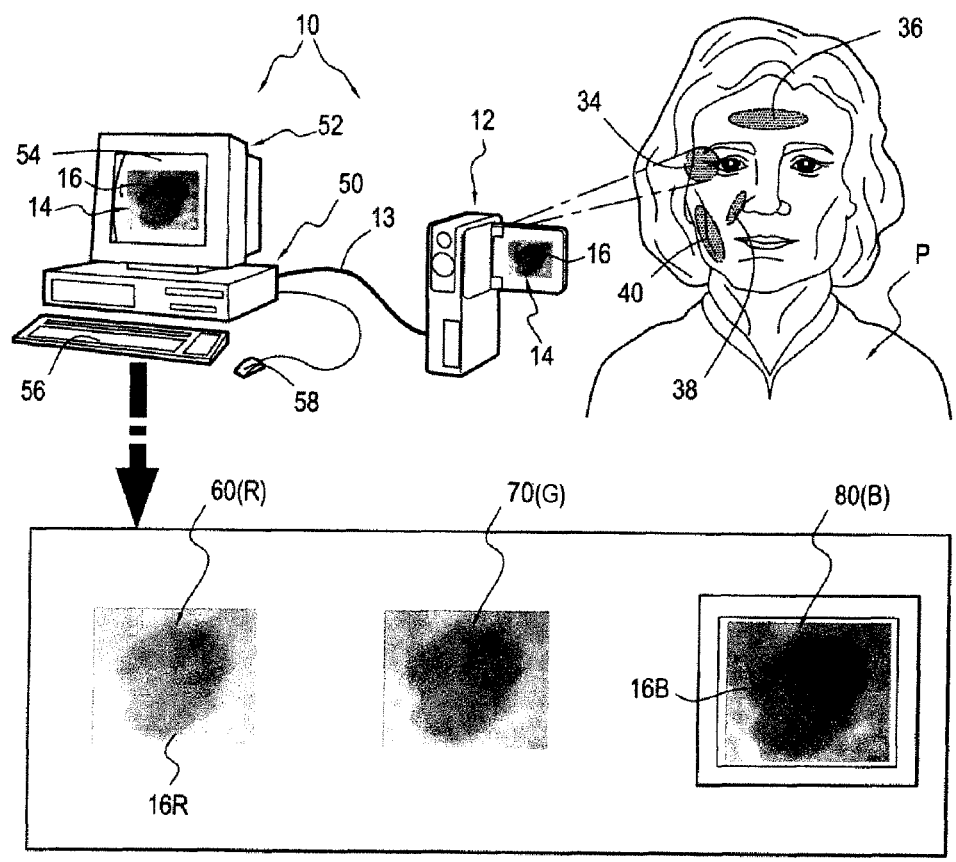
FIG. 1 represents an apparatus for characterizing the skin imperfections of a person, for implementing the method of characterizing skin imperfections described previously and the method of measuring the effectiveness of a treatment of these imperfections with, in this case, according to a first embodiment, the taking of images of an area of skin including at least one pigment spot which is analyzed in particular.
Figure 2:
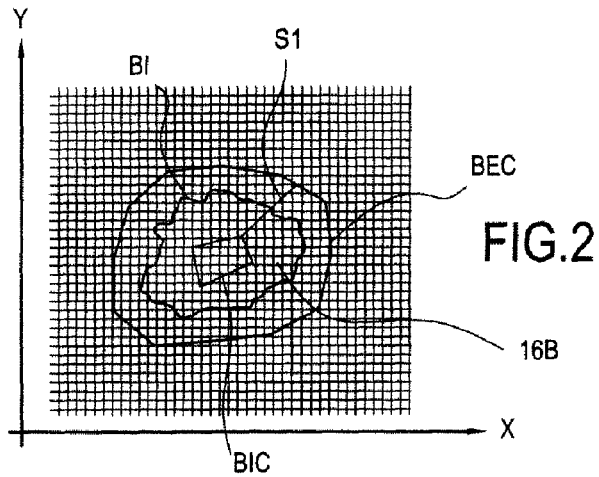
FIG. 2 represents, as an example of imperfection, a pigment spot 16B for which there have been plotted the edge of the imperfection (BI), the crown defined either side of the edge (BI) of the spot by an outer edge (BEC) and an inner edge (BIC), and finally the segment $S_1$, linking the inner edge and the outer edge of the crown, and along which the gray levels are measured.
Figure 3:
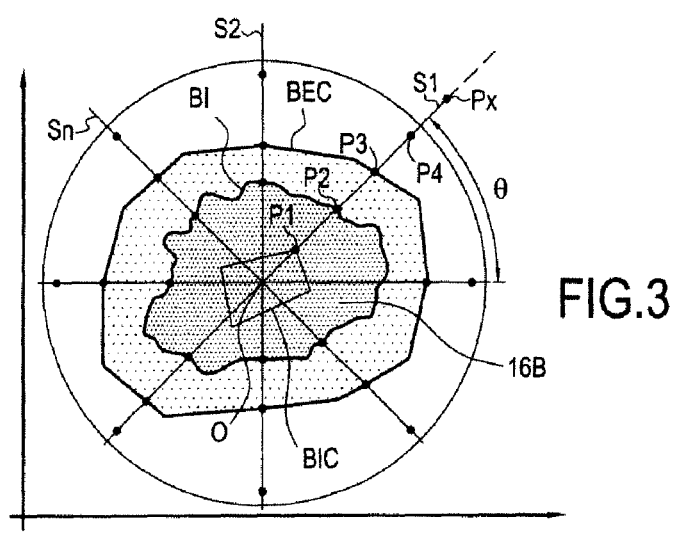
FIG. 3 represents the pigment spot 16B of FIG. 2 for which several straight line segments have been plotted from an origin point O and the points $P_1$, $P_2$, $P_3$ and $P_4$, each corresponding to a pixel of the image, $P_1$ being situated on the inner edge (BIC) of the crown of the spot, $P_2$ being situated on the edge of the spot (BI), $P_3$ being situated on the outer edge (BEC) of the crown of the spot; $P_4$ being situated outside said crown; each segment S1, S2, Sn themselves forming, with the horizontal axis, a predetermined angle that is a multiple of THETA, THETA being in this case equal to 45°.
Figure 4:
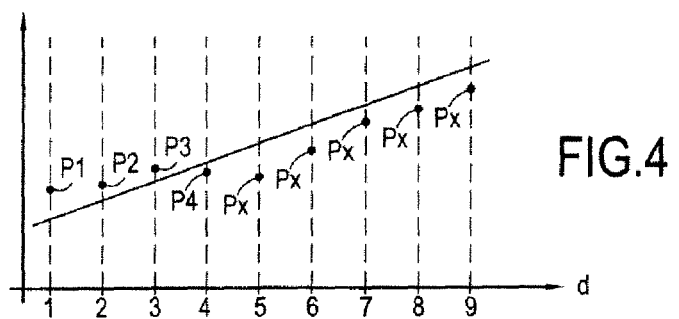
FIG. 4 represents the straight line obtained by adding, to the orthonormed frame of reference (O; x; y), the points P defined for a given segment, including at least $P_1$, $P_2$, $P_3$, $P_4$ ... Px, each point P, corresponding to a pixel of the image, being defined by its pair (x; y); x, on the x axis, representing the distance of the point P relative to the origin point O, and y, on the y axis, representing the gray level measured for said pixel. The slope values of the straight lines obtained from the straight line segments plotted on the extracted plane are used to calculate an average slope value and characterize the imperfection.

According to the Invention—Description of the Apparatus Represented in FIG. 1

Referring to FIG. 1, a currently preferred embodiment of an apparatus according to the invention, represented by the general reference numeral 10, is represented. To ensure accuracy in the positioning of the person P, said person will be seated on a repositioning table, available on the market, for example, under the trade name VISIOFACE, from the company EOTECH in France.

This apparatus 10 is designed to characterize the imperfections 16 of the skin of a person.

According to a particular embodiment of the apparatus according to the invention, there can be provided a device 12 for taking digital color images 14 of at least one determined area of skin 34, 36, 38, 40, said image 14 being defined by a multiplicity of pixels.

The device 12 may be, for example:

either a digital color photographic device with good resolution;

or a digital color camera 12 such as the Fotofinder™ camera from the company DEKA that has an image resolution of 450 000 pixels with 4 volt LED built-in lighting or a digital color camera available on the market notably from the company SONY.

This digital image is then transmitted via transfer means that are well known to those skilled in the art, available on the market, such as an appropriate lead 13, to a digital image processing device.

Also, as is well known to those skilled in the art, the abovementioned digital image processing device is available on the market, for example, in the form of software, such as the image analysis software VISILOG 6.2, that can be installed on a computer 50 linked to said camera 12 by the lead 13. Said computer 50 is naturally combined with a monitor 52 with its screen 54, its keyboard 56 and a mouse 58.

According to the invention, the digital image processing device comprises means of dividing up the digital image into three color planes: red 60, green 70, blue 80, called R, G, B; the digital image processing device also comprises means of extracting just one of these planes or a combination of these planes; in this case, provision is made, for the imperfections 16, to extract the so-called blue plane 80 (B), corresponding to the color blue, the so-called blue imperfection obtained thus being sub-referenced 16B; this image 16B relates to an imperfection of the skin, in this case, according to a first embodiment, a pigment spot; this image may be subjected to a thresholding of the gray levels, thus obtaining a thresholded image, from which to better appreciate the skin imperfections, in this case pigment spots, but they could also be rugae or wrinkles or loose skin.

Also according to the invention, the apparatus also comprises, notably:

means of creating an origin point O in relation to said imperfection, possibly fixed by the operator, from which at least a first straight line segment S1 passing at least partly through an area of the imperfection, in this case the crown of the imperfection defined between $P_1$ and $P_3$, is plotted;

means of creating, on said segment, n points P, denoted $P_1$, $P_2$ ... $P_n$, n being an integer greater than or equal to 2, at least one of these points, denoted $P_1$, being situated within the imperfection;

means of measuring and storing the distance of said point P relative to the origin point O; means of measuring and storing the gray level at said point P;

means of transferring the distances and the gray levels measured and stored for each point P, in an orthonormed frame of reference, in which the x axis represents said distances and the y axis the gray level, or vice versa;

calculation means, built-in or complementing the abovementioned software, are also provided and are used notably to incorporate instructions or measurements given by the operator as stated hereinabove; as well as notably, for each straight line segment, said calculating means comprise calculating means for defining, tracing or plotting a straight line, notably using the least squares method, from said different points $P_1$ to $P_n$ transferred in said orthonormed frame, and for calculating the slope of said obtained straight line, in order to characterize the imperfection.

In a particular embodiment, the calculation means are foreseen for defining, tracing or plotting, from the origin point O, several other straight line segments distinct from the first segment and passing at least partly through an area of the imperfection; then for reproducing the steps f) to i), to obtain as many slope values as there are plotted segments, slope values from which the average is calculated in order to characterize the imperfection.

This characterization of the imperfection from the slope of the straight line obtained takes place as follows:

The lower the gradient deduced from a straight line (or the average value of gradients deduced from several straight lines) becomes, or reduces with respect to a cosmetic or dermatological treatment, the less visible the imperfection becomes.

According to a particular embodiment, the apparatus according to the invention also comprises means of taking into account a thresholding of the gray levels; means of determining the convex envelope of the imperfection and storing an origin point, possibly fixed by the operator, within said convex envelope, before plotting the segment.

According to another particular embodiment of the apparatus according to the invention, the extraction means extract the blue color plane on which the calculation means perform the calculation of the abovementioned parameters.

It has been discovered, according to the invention, that the blue plane 80(B) is preferred because it exhibits the greatest contrast and provides a better view of the skin imperfections.

A mathematical filter provided in the image analysis software can be applied, to the extracted blue plane 80(B), to eliminate the parasitic noise from the image, such as reflection, by obtaining a filtered image.

According to yet another particular embodiment of this apparatus, said apparatus is characterized in that provision is made to take said image of a limited surface area 34, 36, 38, 40 of the skin of the person to be analyzed, on which the calculation means proceed to analyze skin imperfections over the whole of this surface area.

According to an advantageous characteristic of the apparatus according to the invention, said apparatus comprises enlargement means, for example a four-times enlargement when the imperfection is large, such as a pigment spot 16B, in order to enlarge the details. These enlargement means will, also advantageously, be incorporated in said software processing said image obtained by the image-taking appliance 12 enabling an operator to better view the skin imperfections and assess the thresholding of the gray levels with which to eliminate the parasitic elements or artefacts.

According to another advantageous characteristic of the apparatus according to the invention, said apparatus comprises means of taking into account a thresholding of the gray levels, also incorporated in the software, that is to say means with which to eliminate the gray levels below or above a certain predetermined gray level threshold, in order to eliminate parasitic elements, thus producing an image 80B stripped of the parasitic elements.

There is also advantageously provided a second mathematical filtering, also provided in the software, in order to eliminate the minimal areas detected in the preceding thresholding step and that are not of interest, in this case obtaining a thresholded and cleaned image 80, on which the skin imperfections appear very clearly. It is on this final image 80B that the image analysis and calculation steps are preferentially performed.

Thus, in the context of the invention, these image analyses are done on macrophotographs, in particular 80B, of the area of the skin containing an imperfection, for example, notably, for a ruga, a wrinkle or loose skin. For the pigment spots any useful area of the skin, and in particular the hands, the arms or even the legs, will be taken.

The method of quantizing skin imperfections was implemented to quantize the pigment imperfections carried over to example 2 hereinbelow.

Example 2

According to the Invention—Quantizing of the Imperfections: Example of Pigment Spots For this, a sample of 15 volunteers is selected, men and/or women, statistically representative for their pigment spots on the hands.

For the acquisitions, a Fotofinder camera is used (company: DEKA, image-taking device: ¼"CCD (total: 470 000 pixels), built-in lighting: LED, 4 volts), which makes it possible to produce acquisitions enlarged 20 times, to reference the spots, to be positioned in a way that can be reproduced at any time.

Figure 5:
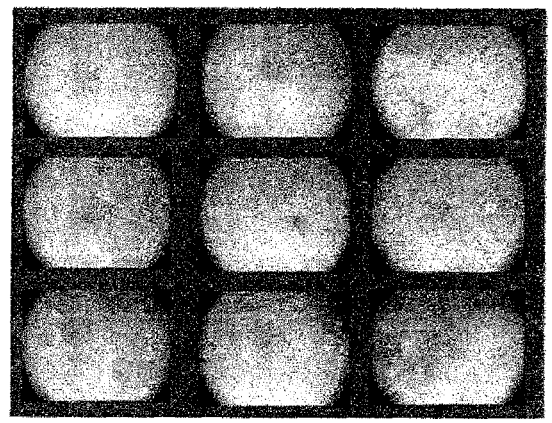
FIG. 5 represents 9 images illustrating pigment spots classified as not very visible.
Figure 6:
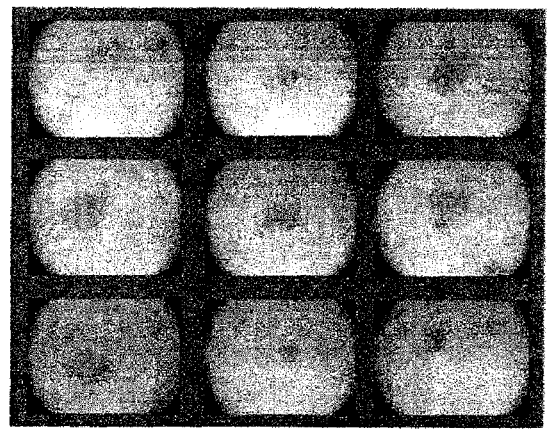
FIG. 6 represents 9 images illustrating pigment spots classified as visible.
Figure 7:
FIG. 7 represents 9 images illustrating pigment spots classified as very visible.

A spot image bank is created, the spots having been rated visually by a beautician and an inventor of the present invention respectively as spots that are not very visible; spots that are visible and spots that are very visible; the plates of 9 images taken in each category are respectively the subject of FIGS. 5, 6 and 7.

Calculation of the Slopes on the Outline of the Spot

The origin O from which the segments are plotted corresponds to the geometrical center of the convex envelope of the cutaneous imperfection.

The segments are plotted at an angle $n\theta$ relative to the horizontal (angle $\theta$). The angle $\theta$ is set for example at 45°. The number of segments plotted is thus equal to eight.

The points P are placed on each segment.

$P_1$ is placed 20 pixels from the edge of the spot, within said spot, $P_3$ is placed 20 pixels from the edge of the spot, outside said spot. The area that the 40 pixels pass through corresponds to the crown of the pigment spot. Thus $P_1$ is situated on the inner edge (BIC) of the crown, $P_2$ is situated on the edge (BI) of the spot, $P_3$ is situated on the outer edge (BEC) of said crown and the point $P_4$ outside the crown. The application determines the gray level at least for each of the 40 pixels along each straight line segment plotted between the points $P_1$ and $P_3$, and possibly beyond the crown to $P_4$.

For each of the eight segments, the slope ($\Delta$ gray levels/$\Delta$ pixels) is calculated for several straight lines supported by segments. The average of the eight slope values obtained in this way characterizes the spot being studied.

The results are summarized in Table I hereinbelow.

TABLE I

Summary of statistical results

| | Spots not very visible | Spots visible | Spots very visible | $P_{class}$ |
|---|---|---|---|---|
| Slope average | 0.65 | 0.97 | 1.05 | $S_{(p<0.01)}$ |

Conclusions:

An analysis of the statistics shows that there is a significant difference between the averages of slopes calculated for spots that are not very visible, on the one hand, and those calculated for spots that are visible or very visible, on the other hand. This method is highly discriminating regarding the spot classes.

The invention also covers all the means that form technical equivalents of the means described, and their various combinations.

Example 3

According to the Invention—Assessing the Effectiveness of a Depigmenting Cosmetic Treatment The images acquired in an effectiveness test performed for an anti-spot product are analyzed.

The anti-spot product is a night cream in the form of an oil-in-water emulsion, comprising 3.3% by weight of magnesium ascorbyl phosphate (source: Showa Denko), an agent with skin lightening properties.

The test modalities are as follows:
Number of volunteers: 14 volunteers, 17 spots studied
Area: hand
Application of the anti-spot composition: 4 product applications, applied topically (0.560 ml), once a day.
Use, as many times as necessary, of a cream for the hands, with a solar protection index (SPF 20).
Measurement time: before the start of the study (T1), then after 4 weeks of treatment
Appliance: Fotofinder, company: DEKA, image-taking device: ¼"CCD (total: 470 000 pixels), built-in lighting: LED, 4 volts.
The slopes are calculated in the same way as in example 2.
For each criterion, the following statistical analyses are carried out for a 5% risk:
overall analysis of the variance
variance analysis for the comparison of the times 1 (before) and t 4 wk
overall analysis of the variance by removing the volunteers with excessive residues. The residues are aberrant values or values that increase the background noise of the analysis.
Results:

| times | sample | average |
|---|---|---|
| T0 | 14 | 0.980 |
| T 4 wk. | 14 | 0.896 |

The test applied (method: 95%, Newman-Keuls) shows a significant difference between the average of the slopes calculated for the images of the spots before treatment then 4 weeks after treatment. The reduction in the average value of the slopes reflects an increasing uniformity of the tone of the skin, visually reflected in an attenuation of the spot.

The invention claimed is:

1. A method consisting of measuring the effectiveness of a cosmetic treatment of skin imperfections by topically applying an active cosmetic agent or a cosmetic composition including said cosmetic agent, comprising at least one step performed by software installed on a computer, the method characterizing at least one imperfection by implementing the following steps:
   a) prior to said cosmetic treatment, taking at least one digital color image of an area of skin including at least one imperfection to be characterized with a digital color image taking device, said digital color image being defined by a multiplicity of pixels, said image being transmitted to the software on the computer;
   b) said software on the computer dividing the digital color image into three color planes: red, green, blue, designated R, G, B;
   c) said software extracting just only the blue plane;
   d) detecting with said software on the computer an imperfection on the extracted blue plane;
   e) defining with said software on the computer, on said blue plane, an origin point O in relation to said imperfection, and plotting from said origin point O at least a first straight line segment (S1, S2, Sn) passing at least partly through an area of the imperfection;
   f) defining with said software on the computer, on said segment (S1, S2, Sn), n points P, denoted $P_1, P_2 \ldots P_n$, n being an integer greater than or equal to 2, at least one of the points, denoted $P_1$, being situated within the imperfection;
   g) automatedly determining with said software on the computer, corresponding to each defined point P, a pair of values (x; y), x being the distance of said point P relative to the origin point O, y being the value of gray level recorded at said point P;
   h) said software on the computer placing each point P defined by its pair (x; y) in an orthonormed frame of reference, in which the x axis represents said distances and the y axis represents the gray level, or vice versa;
   i) said software on the computer defining, tracing or plotting a straight line corresponding to each segment defined at step e), by the least squares method, from the different points P1, to $P_n$ in said orthonormed frame, and automatedly calculating slope of the obtained straight line, in order to characterize the imperfection before treatment;
   j) performing said cosmetic treatment by topically applying said cosmetic active agent or said cosmetic composition including said cosmetic agent on at least said skin imperfection;
   k) taking at least one second color digital image after having performed said cosmetic treatment of said imperfection using at least one said agent, and characterizing with said software on the computer the treated imperfection according to steps a) through i);
   l) said software on the computer including the calculation of the slope or of the average of the slopes obtained from the characterization method according respectively to steps i) and k);
   m) said software on the computer performing a statistical test of the variations of the slopes or of the averages of the above slopes before and after the treatment, thereby enabling an operator to determine significance of the effectiveness of the cosmetic agent or composition.

2. The method of claim 1, wherein each point O, $P_1$, $P_2 \ldots P_n$ corresponds to a pixel of the image.

3. The method of claim 1, comprising thresholding the gray levels to determine the edge of the imperfection; and determining the convex envelope of the imperfection to establish the origin point O within said imperfection, before plotting the segment (S1, S2, Sn).

4. The method of claim 1, comprising determining a particular area, called "crown" of the imperfection, denoted (CI), and plotting the inner edge (BIC) and the outer edge (BEC) of said crown, situated either side of the edge (BI) of said imperfection, at a distance defined by the operator corresponding to a selected number of pixels from the edge of the imperfection (BI).

5. The method of claim 4, comprising defining on said first straight line segment a point $P_1$ situated on the inner edge of the crown (BIC), a point $P_2$ situated on the edge of the imperfection (BI), and a point $P_3$ situated on the outer edge of the crown (BEC).

6. The method of claim 1, comprising defining, tracing or plotting, from the origin point O, several other straight line segments distinct from the first segment defined at step e), and passing at least partly through an area of the imperfection; then reproducing the steps f) to i) to obtain as many slope values as there are plotted segments, and calculating the average of the slope values to characterize the imperfection.

7. The method of claim 6, wherein, from a horizontal axis, defining, tracing or plotting said other straight line segments so that each of them forms, with said horizontal axis, a predetermined angle that is a multiple of THETA, said angle THETA being an angle, defined by the operator, greater than zero and less than 360°.

8. The method of claim 7, wherein the horizontal axis is comprises the first straight line segment.

9. The method of claim 7, wherein THETA is a sub-multiple of 360.

10. The method of claim 7, wherein said angle THETA ranges between 0.1 and 60°, in order to plot segments passing through the imperfection, in a sufficient number to characterize well said imperfection, in average.

11. The method of claim 1, comprising enlarging said image obtained by the digital color image-taking device, to enable an operator to better view the skin imperfections and assess the thresholding of the gray levels with which to eliminate the parasitic elements or artifacts.

12. The method of claim 1, comprising selecting a limited surface area of the skin of the person on which the skin imperfections are analyzed over the whole of this surface area.

13. The method of claim 1, comprising storing one image or a plurality of images of the skin of one and the same person on a digital data storage device.

14. The method of claim 1, wherein the imperfection results from the intrinsic skin ageing, from the extrinsic skin ageing, from a cutaneous dyschromia, from a skin irritation or a skin infection.

15. The method of claim 1, wherein the imperfection is selected from the group consisting of:
- a cutaneous dyschromia in the form of at least one spot of different color from the healthy skin because of an abnormal pigmentation,
- a photodermatose,
- a keratose,
- a senile lentigo or aging spot,
- a solar lentigo,
- a persistent effect of burns
- a skin wound or scar,
- a spot due to allergic or phototoxic reactions,
- a depigmented area induced by a leucodermia,
- a ruga,
- a wrinkle,
- a shadow, and
- an area of loose skin.

16. The method of claim 1, wherein the parameters of the second image of the same area of skin obtained after treatment are compared against the parameters of the first skin image before treatment.

17. The method of claim 1, wherein the effectiveness of said active cosmetic agent or of said cosmetic composition including said active cosmetic agent is assessed over a panel of people from a group representative of a given age category, to determine the significance of the effectiveness of said active agent or of said composition with respect to said skin imperfection.

18. A method consisting of measuring the effectiveness of a cosmetic treatment of skin imperfections by topically applying an active cosmetic agent or a cosmetic composition including said cosmetic agent, comprising at least one step performed by software installed on a computer, the method characterizing at least one imperfection by implementing the following steps:
a) prior to said cosmetic treatment, taking at least one digital image of an area of skin including at least one imperfection to be characterized with a digital color image taking device, said image being defined by a multiplicity of pixels, said image being transmitted to said software on said computer;
b) dividing with the software on said computer, the digital image into three color planes: red, green, blue, designated R, G, B;
c) said software on the computer extracting just the blue plane;
d) detecting an imperfection on the extracted blue plane;
e) defining with said software on said computer, on said extracted blue plane, an origin point O in relation to said imperfection, and plotting from said origin point O at least a first straight line segment (S1, S2, Sn) passing at least partly through an area of the imperfection;
f) defining with said software on said computer, on said segment (S1, S2, Sn), n points P, denoted $P_1, P_2 \ldots P_n$, n being an integer greater than or equal to 2, at least one of the points, denoted $P_1$, being situated within the imperfection;
g) determining with said software on said computer, corresponding to each defined point P, a pair of values (x; y), x being the distance of said point P relative origin point O, y being the value of gray level recorded at said point P;
h) said software on said computer placing each point P defined by each point P's pair (x; y) in an orthonormed frame of reference, in which the x axis represents said distances and the y axis represents the gray level, or vice versa;
i) said software on said computer defining, tracing or plotting a straight line corresponding to each segment defined at step e), by the least squares method, from the different points P1, to $P_n$ in said orthonormed frame, and automatedly calculating the slope of the obtained straight line, in order to characterize the imperfection before treatment;
j) performing said cosmetic treatment by topically applying said cosmetic active agent or said cosmetic composition including said cosmetic agent on at least said skin imperfection;
k) taking at least one color digital image after having performed a cosmetic treatment of said imperfection using at least one said agent, characterizing with said software on said computer the treated imperfection according to steps a) through i);
l) said software on said computer including the calculation of the slope or of the average of the slopes obtained from the characterization method according respectively to steps i) and k);
m) said software on said computer performing a statistical test of the variations of the slopes or of the averages of the above slopes before and after the treatment, thereby enabling the operator to better determine the significant nature of the effectiveness of said treatment;
wherein a significant treatment is obtained when a diagnosis error probability is less than or equal to 5%.

19. A method of performing a cosmetic treatment consisting of measuring the effectiveness of the attenuation or the masking of skin imperfections, by topically applying a cosmetic staining composition on skin, comprising the following steps:
taking at least one first digital image using a digital color-image taking device and a digital image processing device, before applying the staining composition, of at least one predetermined area of skin in order to determine the reference parameters of the skin before the application of the staining composition while taking into account at least the slope or the average of the above slopes as determined according to following steps; at least one step being performed by software on a computer, the method comprising:
a) prior to said cosmetic treatment, taking at least one color digital image of an area of skin including at least one imperfection to be characterized with the digital color-image taking device, said image being defined by a multiplicity of pixels, said image being automatedly transmitted to said software on said computer;
b) dividing with said software on said computer the digital image into three color planes: red, green, blue, designated R, G, B;
c) extracting with said software on said computer just the blue plane;
d) detecting with said software on said computer an imperfection on the extracted blue plane;
e) defining with said software on said computer, on said extracted blue plane, an origin point O in relation to said imperfection, and automatedly plotting from said origin point O at least a first straight line segment (S1, S2, Sn) passing at least partly through an area of the imperfection;
f) automatedly defining with said software on said computer, on said segment (S1, S2, Sn), n points P, denoted $P_1, P_2 \ldots P_n$, n being an integer greater than or equal to 2, at least one of the points, denoted $P_1$, being situated within the imperfection;
g) determining with said software on said computer, corresponding to each defined point P, a pair of values (x; y), x being the distance of said point P relative to the origin point O, y being the value of gray level recorded at said point P;
h) said software on said computer placing each point P defined by each point P's pair (x; y) in an orthonormed frame of reference, in which the x axis represents said distances and the y axis represents the gray level, or vice versa;
i) said software on said computer defining, tracing or plotting with a straight line corresponding to each segment defined at step e), by the least squares method, from the different points P1, to $P_n$ in said orthonormed frame, and automatedly calculating the slope of the obtained straight line, in order to characterize the imperfection before treatment;
j) performing said cosmetic treatment by topically applying said cosmetic staining composition on at least said skin imperfections;
k) taking at least one second image after the staining composition is applied, and the same parameters are determined with said software on said computer according to steps a) through k);
l) said software on said computer including calculation of the slope or of the average of the slopes obtained from the method according respectively to steps i) and j);
l) said software on said computer performing a statistical test of variations of the slopes or of the averages of the slopes before and after treatment, thereby enabling the operator to better determine a significant nature of the effectiveness of said cosmetic staining composition.

* * * * *